(12) United States Patent
Friebe et al.

(10) Patent No.: US 10,500,549 B2
(45) Date of Patent: Dec. 10, 2019

(54) DIALYSIS MEMBRANE AND METHOD FOR ITS PRODUCTION

(71) Applicant: B. BRAUN AVITUM AG, Melsungen (DE)

(72) Inventors: Alexander Friebe, Freital (DE); Roland Napierala, Werther (DE); Angela Baier-Goschütz, Bad-Gottleuba-Berggiesshübel (DE); Juliane Gäbler, Pulsnitz (DE); Mathias Ulbricht, Essen (DE); Clélia Jade Eléonore Victoria Emin, Bochum (DE)

(73) Assignee: B. Braun Avitum AG (DE)

( * ) Notice: Subject to any disclaimer, the term of this patent is extended or adjusted under 35 U.S.C. 154(b) by 258 days.

(21) Appl. No.: 15/436,135

(22) Filed: Feb. 17, 2017

(65) Prior Publication Data

US 2017/0232405 A1 Aug. 17, 2017

(30) Foreign Application Priority Data

Feb. 17, 2016 (DE) .................. 10 2016 102 782

(51) Int. Cl.
| | |
|---|---|
| *B01D 71/68* | (2006.01) |
| *B01D 69/06* | (2006.01) |
| *B01D 69/08* | (2006.01) |
| *B01D 69/12* | (2006.01) |
| *B01D 71/12* | (2006.01) |
| *B01D 71/60* | (2006.01) |
| *B01D 67/00* | (2006.01) |
| *B01J 41/13* | (2017.01) |
| *B32B 27/28* | (2006.01) |
| *B01D 69/02* | (2006.01) |
| *B01D 69/10* | (2006.01) |
| *B01D 61/24* | (2006.01) |
| *B01D 63/02* | (2006.01) |
| *B01D 63/08* | (2006.01) |
| *A61M 1/16* | (2006.01) |

(52) U.S. Cl.
CPC ......... *B01D 71/68* (2013.01); *B01D 67/0009* (2013.01); *B01D 67/0013* (2013.01); *B01D 67/0093* (2013.01); *B01D 69/02* (2013.01); *B01D 69/06* (2013.01); *B01D 69/08* (2013.01); *B01D 69/10* (2013.01); *B01D 69/12* (2013.01); *B01D 71/12* (2013.01); *B01D 71/60* (2013.01); *B01J 41/13* (2017.01); *B32B 27/286* (2013.01); *A61M 1/16* (2013.01); *B01D 61/243* (2013.01); *B01D 63/02* (2013.01); *B01D 63/08* (2013.01); *B01D 2323/02* (2013.01); *B01D 2323/36* (2013.01); *B01D 2325/04* (2013.01); *B01D 2325/14* (2013.01); *B01D 2325/16* (2013.01); *B01D 2325/36* (2013.01)

(58) Field of Classification Search
CPC . A61M 1/16; B01D 2323/02; B01D 2323/36; B01D 2325/04; B01D 2325/14; B01D 2325/16; B01D 2325/36; B01D 61/243; B01D 63/02; B01D 63/08; B01D 67/0009; B01D 67/0013; B01D 67/0093; B01D 69/02; B01D 69/06; B01D 69/08; B01D 69/10; B01D 69/12; B01D 71/12; B01D 71/60; B01D 71/68; B01J 41/13; B32B 27/286
See application file for complete search history.

(56) References Cited

U.S. PATENT DOCUMENTS

| | | | |
|---|---|---|---|
| 6,042,783 | A | 3/2000 | Nagamatsu et al. |
| 2002/0165503 | A1 | 11/2002 | Morris et al. |
| 2006/0195064 | A1 | 8/2006 | Plahey et al. |
| 2008/0000828 | A1 | 1/2008 | Wechs et al. |
| 2013/0277878 | A1 | 10/2013 | Gohl et al. |

FOREIGN PATENT DOCUMENTS

| | | |
|---|---|---|
| CN | 201669064 U | 12/2010 |
| DE | 4243996 A1 | 6/1994 |
| DE | 69132403 T2 | 3/2001 |
| DE | 102004008220 B4 | 1/2006 |
| EP | 0480039 B1 | 4/1992 |
| EP | 1634611 B1 | 3/2006 |
| WO | 03020425 A1 | 3/2003 |

(Continued)

OTHER PUBLICATIONS

European Search Report with English language machine translation for Application No. 17156674.8, dated Aug. 25, 2017, 18 pages.

(Continued)

*Primary Examiner* — John Kim (74) *Attorney, Agent, or Firm* — RatnerPrestia (57) ABSTRACT

A membrane for the purification of blood, or a dialysis membrane, in hollow-fiber membrane or flat membrane geometry, made of a composite assembled from at least a base membrane based on at least one polysulfone or a polyphenylsulfone with at least one pore-forming hydrophilic additive and at least one functional layer arranged on the base membrane, whereby the functional layer is formed from at least one polymeric polycationic bonding agent and at least one polymeric polyanion, whereby the base membrane is made of a material which is selected from: a polysulfone [PSU], a sulfonated polysulfone [SPSU], a polyethersulfone [PES], a sulfonated polyethersulfone [SPES], a polyphenylsulfone [PPSU], a sulfonated polyphenylsulfone [SPPSU]; and mixtures of these.

11 Claims, 6 Drawing Sheets

(56) References Cited

FOREIGN PATENT DOCUMENTS

| WO | 2013156597 A1 | 10/2013 |
| WO | 2013156598 A1 | 10/2013 |

OTHER PUBLICATIONS

Filiz, Yasar Mahlicli, et al., "Surface modification of polysulfone based hemodialysis membranes with layer by layer self assembly of polyethyleneimine/alginate-heparin: a simple polyelectrolyte blend approach for heparin immobilization", Journal of Materials Science: Materials in Medicine, Bd. 24, No. 2, pp. 533-546, Feb. 1, 2013, 14 pages.

Aravind, Usha K., et al., "Transport studies of BSA, lysozyme and ovalbumin through chitosan/polystyrene sulfonate multilayer membrane", Journal of Membrane Science, Elsevier BV, NL, Bd. 299, No. 1-2, pp. 146-155, Jun. 22, 2007, 10 pages.

Krasemann, Lutz, et al., "Self-assembled polyelectrolyte multilayer membranes with highly improved pervaporation Separation of ehtanol/water mixtures", Journal of Membrane Science, Elsevier BV, NL, Bd. 181, No. 2, pp. 221-228, Jan. 30, 2001, 8 pages.

Heinrich, S., et al., "Nanotechnology for health," 2010, vol. 2, 3 pages.

Blanco, J.F., et al., "Sulfonation of polysulfones: Suitability of the sulfonated materials for asymmetric membrane preparation," 2002, vol. 84, pp. 2461-2473, Journal of Applied Polymer Science.

Li, Y., et al., "Exploration of highly sulfonated polyethersulfone (SPES) as a membrane material with the aid of dual-layer hollow fiber fabrication technology for protein separation," 2008, vol. 309, pp. 45-55, Journal of Membrane Science.

Mahlicli, F.Y., et al., "Surface modification of polysulfone based hemodialysis membranes with layer by layer self assembly of polyethyleneimine/alginate-heparin: a simple polyelectrolyte blend approach for heparin immobilization," 2013, vol. 24, pp. 533-546, Journal of Materials Science.

Malaisamy, R., et al., "High-flux nanofiltration membranes prepared by adsorption of multilayer polyelectrolyte membranes on polymeric supports," 2005, vol. 21, No. 23, pp. 10587-10592, Langmuir.

Kopec, K.K., et al., "Tailoring the surface charge of an ultrafiltration hollow fiber by addition of a polyanion to the coagulation bore liquid," 2011, vol. 369, pp. 59-67, Journal of Membrane Science.

Kochan, J., et al., "Properties of polyethersulfone ultrafiltration membranes modified by polyelectrolytes," 2010, vol. 250, pp. 1008-1010, Desalination.

German Examination Report for German Application No. 10 2016 102 782.0, dated Apr. 12, 2016, including English translation, 8 pages.

DIALYSIS MEMBRANE AND METHOD FOR ITS PRODUCTION

CROSS REFERENCE TO RELATED APPLICATIONS

This application claims priority to German application DE 10 2016 102 782.0 filed Feb. 17, 2016, the contents of such application being incorporated by reference herein.

FIELD OF THE INVENTION

The present invention concerns a dialysis membrane, a method for the production of the same and a dialysis membrane module.

The following polymer abbreviations are used in the context of the present invention:

| Abbreviation | Polymer |
| --- | --- |
| DEXS | Dextran sulphate |
| PA | Polyamide |
| PAA | Polyacrylic acid |
| PAN | Polyacrylonitrile |
| PC | Polycarbonate |
| PEG* | Polyethylene glycol |
| PEI | Polyethylenimine |
| PEO* | Polyethylene oxide |
| PES | Polyphenylsulfone |
| PMMA | Polymethyl methacrylate |
| PPSU | Polyphenylsulfone |
| PUR | Polyurethane |
| PSU | Polysulfone |
| PVP | Polyvinylpyrrolidone |
| SPES | Sulfonated polyethersulfone |
| SPSU | Sulfonated polysulfone |
| SPPSU | Sulfonated polyphenylsulfone |

*PEG and PEO are essentially the same molecule. For the purposes of the present invention, PEG is regarded as a polymer with a molar mass of less than 100 kDa. A polymer with a molar mass from 100 kDa is referred to as PEO.

BACKGROUND OF THE INVENTION

Dialysis for the treatment of patients after kidney failure was carried out successfully for the first time in the 1940s. Dialysis membranes have advanced rapidly since then. In particular, it was possible to achieve miniaturization from the rotating-drum kidney to the plate dialyzer and on to today's modern hollow-fibre dialyzer.

Nowadays membranes for hollow-fibre dialyzers are produced on an industrial scale in large numbers and in high, reproducible quality; they are generally offered as disposable systems in the form of dialysis membrane modules. In particular, nano-controlled spinning technologies have resulted in a considerable improvement. Dialysis membranes made of plastics are now the standard for low-cost therapy. Further development of dialysis membranes aim to approach the natural function of the glomerular membrane of the human kidney even further so as to ensure optimum treatment in the event of renal insufficiency or complete renal failure in order to compensate for the lack of kidneys as a result of surgery or trauma.

In the advancement of membranes suitable for dialysis, the focus is on a high degree of biocompatibility and high or configurable water permeability, while at the same time achieving the therapeutically desired separation effect. From the clinical point of view, dialysis treatment continues to be of growing importance since the number of patients to be treated worldwide is increasing constantly, firstly as a result of an ageing population and secondly due to the economic possibilities and availability of treatment for renal insufficiency, which will likewise increase in the developing countries in the future.

DESCRIPTION OF THE RELATED ART

In addition to this, the aim is to achieve a downscaling of dialyzers, which would mean the long-term objective of achieving complete miniaturization of dialysis membranes down to a kidney implant consuming very little energy [see Stefan Heinrich, H. Oliver Pfirrmann, Nanotechnologie für die Gesundheit, Gesundheitsvorsorge im Wandel, 2, 12 (2010)].

The state of the art describes a wide range of membranes, partly for ultrafiltration and partly for hemodialysis.

For example, US 2013/0 277 878 A1 describes a method for producing a hollow-fibre dialysis membrane with a spinning technique with phase inversion.

Such membranes are structured from at least one hydrophilic and at least one hydrophobic polymer. US 2013/0 277 878 A1 discloses as suitable hydrophilic polymers polyvinylpyrrolidone (PVP), polyethylene glycol, polyglycol monoester, water-soluble cellulose derivatives, polysorbate and polyethylene oxide/polypropylene oxide copolymers.

The hydrophobic polymers can be the following according to US 2013/0 277 878 A1: polyamides (PA), polyacrylic acids (PAA), polyarylethersulfones (PAES), polyethersulfones (PES), polysulfones (PSU), polyarylsulfone (PASU), polycarbonates (PC), polyurethanes (PUR).

Document DE 10 2004 008 220 B4 discloses hydrophilic hollow-fibre membranes for hemodialysis. The material named is a first synthetic polymer which can be a hydrophobic polymer, including PSU and/or PES. The composite membranes of DE 10 2004 008 220 B4 contain a hydrophilic second polymer which can be selected from the group: PVP, PEG, polyvinyl alcohol, polyglycol monoester, polysorbate, carboxymethyl cellulose or a mixture or copolymer of these polymers.

Furthermore, for the so-called high-flux dialysis membranes of DE 10 2004 008 220 B4, an ultrafiltration rate in albumin solution is disclosed in the range of 25 to 60 ml/(h×m$^2$×mm Hg) and a sieving coefficient for cytochrome c of at least 0.8 in combination with a sieving coefficient for albumin of maximum 0.005, whereby the hollow-fibre membranes of DE 10 2004 008 220 B4 are free of glycerine and other additives which stabilize the pores in the membrane wall.

Furthermore, U.S. Pat. No. 6,042,783 A discloses a hollow-fibre membrane made of a PSU resin for which the permeation ratio—not described in further detail—is ≤1% for all proteins.

Furthermore, document EP 1 634 611 B1 discloses a blood purifier with a hollow-fibre membrane made of a polymer of the polysulfone type and PVP, wherein a maximum of 10 ppm PVP is aqueous elutable out of one gram of hollow-fibre membrane. The polymers described of the polysulfone type are polysulfone and polyethersulfone.

Furthermore, CN 201 669 064 U discloses a base membrane made of a polysulfone with a "polyose" film for medical purposes which is not further characterized.

Furthermore, WO 2013/156 598 A1, for example, discloses ultrafiltration membranes which contain at least one substrate layer based on a partially sulfonated polyethersulfone as a polymer. The polysulfones used in the state of the art are solely polyethersulfones which can be partially sulfonated.

Furthermore, WO 2013/156 597 A1 discloses nanofiltration membranes made of a composite of a substrate layer, at least a partially sulfonated polyethersulfone and at least a film layer made of a cationic polymer, whereby cationic polymers are disclosed which contain trimethyl ammonium salts as side groups.

In addition to the patent literature listed above, there is also a range of scientific literature dealing with membranes and in particular with membranes suitable for hemodialysis.

For example, Blanco et al. (2002): J Appl Polymer Sci 84, 2461 describes the broad use of polysulfones to make asymmetrical membranes for ultrafiltration and nanofiltration. In concrete terms, the use of polysulfone as a medium and polyamide as a functional layer for asymmetrical membranes is described. Blanco et al. also show that sulfonating can increase the hydrophily of the PSU polymers which are in themselves hydrophobic.

Furthermore, Li et al. (2008): J Membrane Sci 309, 45 describe dual-layer hollow-fibre membranes for protein separation using the example of BSA/Hb. Polyethersulfone is used for the porous inner supporting layer and the outer layer is made of sulfone, whereby the polyethersulfone layer was stable enough to support the sulfonated polyethersulfone layer so that it was possible to use the membranes successfully for protein separation.

Mahlicli et al. (2013): J Mater Sci: Med 24, 533 disclose a surface modification of dialysis membranes based on polysulfones using layer-by-layer (LbL) self-assembly of polyethylenimine/alginate-heparin layers According to Mahlicli et al., a polysulfone is initially sulfonated and then a blend of polysulfone and sulfonated polysulfone is poured out on a glass plate to form a flat supporting membrane, whereby the solvent is specified as N-Methyl-2-pyrrolidone.

The LbL assembly is carried out according to Mahlicli et al. on the PSU/SPSU membrane which is negatively charged by the $SO_3$ groups introduced. For this purpose the membrane was immersed in a solution of polyethylenimine [PEI] and incubated for 10 minutes. After setting the pH value to a sufficient level so as to create the protonated form of the PEI, surplus PEI is rinsed out and the membrane is immersed in an alginate solution where it is incubated for 10 minutes. Surplus alginate is removed with rinsing The alternating PEI/alginate immersion is repeated several times so as to produce a multi-layer assembly. As the final layer, the support membrane thus coated with PEI-alginate complexes is then either immersed in a pure heparin solution or else immersed in alginate/heparin solution so as to obtain as the final layer a pure heparin layer or a mixed layer of alginate and heparin. According to Mahlicli et al. the permeation properties of the membranes produced by the authors for urea, vitamin $B_{12}$ and lysozyme are comparable with those of industrial AN69 dialysis membranes. The plasma protein adsorption of the membranes was significantly reduced. Likewise, thrombocyte activation as a consequence of the anticoagulative coating was considerably reduced.

In addition, Malaisamy et al. (2005): Langmuir 21, 10587 describe nanofiltration membranes with polyethersulfone as the support and an LbL coating with polystyrene sulfonate [PSS] and protonated poly(allylamine) [PAH] and/or poly(diallydimethylammonium chloride) [PDADMAC].

Kopec et al. (2011): J Membrane Sci 369, 59 describe the process of designing membrane surface charges with LbL technique taking the example of support membranes made of polyimides and coatings made of sulfonated poly(ether ketone) [SPEEK] and supports made of PSU with SPEEK coating. The membranes are configured as hollow-fibre membranes for ultrafiltration.

Finally, Kochan et al. (2010): Desalination 250, 1008 describe hollow-fibre membranes made of polyethersulfones whose surface is modified with the LbL method with a polyelectrolyte, in particular polyethylenimine and polystyrene sulfonate. The PEI used is a commercial PEI with a molar mass of 57 kDa. The membranes of this state of the art can be used for waste water treatment. When the molecular weight cut-off value was tested with dextran, it transpired according to Kochan et al. that a considerable increase in the retention for dextran was observed in the coated membranes while at the same time permeability was reduced.

SUMMARY OF THE INVENTION

The present invention concerns, for example, a dialysis membrane in hollow-fibre membrane or flat membrane geometry made of a composite assembled from at least one base membrane based on at least one polysulfone with at least one pore-forming hydrophilic additive and at least one functional layer arranged on the base membrane, whereby the functional layer is formed from at least one polymeric polycationic bonding agent and at least one polymeric polyanion, wherein the base membrane is formed from a material which is selected from: a polysulfone [PSU], a sulfonated polysulfone [SPSU], a polyethersulfone [PES], a sulfonated polyethersulfone [SPES], a polyphenylsulfone [PPSU], a sulfonated polyphenylsulfone [SPPSU]; and mixtures of these; the polycationic bonding agent is a polyethylenimine [PEI], for example with a molecular mass of between 1 kDa and 2 MDa ($M_w$), in particular approx. 2.0 kDa, approx. 25 kDa or approx. 750 kDa ($M_w$), chitosan, e.g. with a molecular mass of between 30 kDa and 750 kDa ($M_w$), polylysine, e.g. with a molecular mass of between 15 kDa and 300 kDa ($M_w$) (e.g. poly L-lysine sigma), polyarginine e.g. with a molecular mass of between 1.9 kDa and 38.5 kDa ($M_w$) (for example n-butyl-poly-L-arginine hydrochloride) or polyornithine, for example with a molecular mass of between 1.5 kDa and 30.1 kDa ($M_w$); the polyanion is a sulfated polysaccharide which is selected from: a dextran sulfate [DEXS], for example with a molecular mass of 15 kDa to 1 MDa ($M_w$), in particular approx. 500 kDa ($M_w$), a sulfated chitosan, e.g. with a molecular mass of 30 kDa to 750 kDa ($M_w$); a cellulose sulfate, e.g. with a molecular mass of between 20 kDa and 1 MDa ($M_w$), preferably approx. 100 kDa ($M_w$); or mixtures of these; and whereby the pore-forming hydrophilic additive is selected from: polyvinylpyrrolidone [PVP], e.g. with a molecular mass of between 1 kDa and 2,2 MDa ($M_w$), in particular approx. 1.1 MDa ($M_w$), a short-chain glycol with 2 to 10 atoms, triethylene glycol, propylene glycol, polyethylene glycol [PEG]/polyethylene oxide [PEO], for example with a molecular mass of between 600 Da and 500 kDa ($M_w$), in particular approx. 8 kDa ($M_w$) or approx. 10 kDa ($M_w$); and mixtures of these.

Typically, the polysulfones used according to aspects of the invention exhibit the following number average ($M_n$) and weight average ($M_w$) molecular mass range:
polysulfone [PSU]: $M_n$ 16-22 kDa, $M_w$ 40-85 kDa,
sulfonated polysulfone [SPSU]: $M_n$ 27-32 kDa, $M_w$ 50-55 kDa,
polyethersulfone [PES]: $M_n$ 16-22 kDa, $M_w$ 30-75 kDa,
sulfonated polyethersulfone [SPES]: $M_n$ 18-22 kDa, $M_w$ 30-35 kDa, polyphenylsulfone [PPSU]: $M_n$ 22 kDa, $M_w$ 52-55 kDa, and sulfonated polyphenylsulfone [SPPSU]: $M_n$ 17-21 kDa, $M_w$ 47-53 kDa.

A preferred embodiment of the present invention is a dialysis membrane in which the SPSU exhibits sulfonation degree of 0.1 to 20 weight %, in relation to the weight of the unsulfonated PSU; and/or the SPES exhibits a sulfonation degree of 0.1 to 20 weight %, in relation to the weight of the unsulfonated PES; and/or the SPPSU exhibits a sulfonation degree of 0.1 to 20 weight %, in relation to the weight of the unsulfonated PPSU.

The weight percentages are calculated for sulfonated SPES and SPSU from NMR analyses. The samples for this purpose were dissolved in deuterated dimethyl sulfoxide or deuterated chloroform and the NMR spectra were measured using a 300 MHz or a 500 MHz NMR device (Bruker). Based on the results, the molar ratios between non-sulfonated and sulfonated repetition units ($M_{PES}$=232 g/mol; $M_{SPES}$=312 g/mol), the sulfonation degrees of SPES3, SPES2 and SPES4 were determined at 1.1; 3,6 and 14.1 weight % respectively (specification range from 0.1 to 20 weight %).

SPSUA, SPSUB with 9.3 and 13.4 weight % (unit: $M_{PSU}$=442 g/mol; $M_{SPSU}$=522 g/mol); specification range of 0.1 to 20 weight %

Furthermore the specification for sPPSU is related to the mass content of the sulfonated monomer 4,4' Dichlordiphenyl sulfone [sDCDPS].

The present invention involves the capability to produce advantageous dialysis membranes, whereby the SPSU exhibits a sulfonation degree of 9.3 or 13.4 weight %, in relation to the weight of the unsulfonated PSU.

Such dialysis membranes are likewise preferable in which the SPES exhibits a sulfonation degree of 1.1; 3.6 or 14.1 weight %, in relation to the weight of the unsulfonated PES.

In terms of dialysis membranes which contain SPPSU, preference is given to those which exhibit a sulfonation degree of 1.0, 2.0, 10.1 or 14.7 weight %, in relation to the weight of the unsulfonated PPSU.

Preferred additives have been shown to be polyethylene glycol with a molecular mass of 600 Da to 500 kDa ($M_w$), in particular approx. 8 kDa ($M_w$) or 10 kDa ($M_n$) and/or a PVP with a molecular mass of 1 kDa to 2.2 MDa ($M_w$), in particular approx. 1.1 MDa ($M_w$).

The preferred bonding agent for use in connection with the present invention is a PEI with a molecular mass of between 1 kDa and 2 MDa ($M_w$), in particular approx. 2 kDa, preferably approx. 25 kDa, preferably approx. 750 kDa ($M_w$) or a C2 to C8-dialkanal cross-linked, in particular 1,5-pentanedial cross-linked, high-molecular PEI. In particular, PEI with a molar mass of 750 kDa is commercially available, while the specially synthetically cross-linked PEI polymers can be configured in terms of their properties, in particular their molecule size, for example via the degree of polymerization and the choice of cross-linking agent.

For the purpose of LbL coating, the preferred polysaccharide for use in connection with the present invention is a dextran sulfate with a molecular mass ($M_w$) of 15 kDa to 1 MDa, in particular approx. 500 kDa and/or a sulfated chitosan with a molecular mass of 30 kDa to 750 kDa; or mixtures of these.

In the preferred embodiments of the present invention, such dialysis membranes are used in which the pore-forming additive is selected from: a PVP with a molecular mass of approx. 1.1 MDa, glycerine, a PEG/polyethylene oxide [PEO] with a molecular mass of 600 Da to 500 kDa ($M_w$), in particular approx. 10 kDa ($M_n$) or 8 kDa ($M_w$) or a 3-component mixture of these.

The preferred dialysis membranes exhibit a water permeability of 10 to 2,000 L/bar*h*m$^2$ and a sieving coefficient (@22±2° C.) for bovine serum albumin [BSA] in the range of 0.5 to 0.0001 and a molecular mass cut-off value of 20 to 50 kDa.

A further preferred embodiment of the dialysis membrane according to aspects of the invention is characterized in that the polyethylene glycol/polyethylene oxide exhibits a molecular mass of 600 Da to 500 kDa ($M_w$), in particular approx. 8 kDa ($M_w$) or approx. 10 kDa ($M_n$), and/or the PVP exhibits a molecular mass of 1 kDa to 2.2 MDa ($M_w$), in particular approx. 1.1 MDa ($M_w$).

Another preferred embodiment of the dialysis membrane according to aspects of the invention is characterized in that the bonding agent is:
  a polyethylenimine [PEI] with a molecular mass ($M_w$) of 1 kDa to 2 MDa, a
  chitosan with a molecular mass ($M_w$) of 40 to 220 kDa,
  a polylysine with a molecular mass ($M_w$) of 15 to 300 kDa,
  a polyarginine with a molecular mass ($M_w$) of 1.9 to 38.5 kDa,
  a polyornithine with a molecular mass ($M_w$) of 1.5 kDa to 30.1 kDa, or a mixture of these.

The above-mentioned dialysis membrane is furthermore preferably characterized in that the bonding agent PEI has a molecular mass ($M_w$) of approx. 2 kDa, in particular approx. 25 kDa, preferably approx. 750 kDa, or is a C2 to C8-dialkanal cross-linked, in particular 1.5-pentanedial cross-linked, high-molecular PEI.

Another preferred embodiment of the dialysis membrane according to aspects of the invention is characterized in that the polysaccharide is a dextran sulfate with a molecular mass ($M_w$) of approx. 500 kDa and/or a sulfated chitosan with a molecular mass ($M_w$) of 30 kDa to 750 kDa.

Another preferred embodiment of the dialysis membrane according to aspects of the invention is wherein the pore-forming additive is selected from: a PVP with a molecular mass ($M_w$) of 1 kDa to 2,2 MDa, in particular approx. 1.1 MDa, glycerine, propylene glycol, triethylene glycol, a PEG/PEO with a molecular mass ($M_w$) of 600 Da to 500 kDa, in particular 8 to 10 kDa or a multi-component mixture of these.

Another preferred embodiment of the dialysis membrane according to aspects of the invention is wherein the contact angle exhibits a value of 20 to 70°, thereby ensuring very good wettability of the membranes (hydrophily).

The present invention likewise discloses a method for producing a dialysis membrane in hollow-fibre or flat-membrane geometry, whereby
  a) a casting or spinning solution is made for the production of a dialysis membrane out of at least one polysulfone, which is selected from: a polysulfone [PSU], a sulfonated polysulfone SPSU], a polyethersulfone [PES], a sulfonated polyethersulfone [SPES], a polyphenylsulfone [PPSU], a sulfonated polyphenylsulfone [SPPSU]; and mixtures of these; and at least one a pore-forming hydrophilic additive in at least one organic solvent, selected from N,N-dimethylacetamide, dimethyl sulfoxide, N-Methyl-2-pyrrolidone or N-Ethyl-2-pyrrolidone; and
  b) the polymer mixture solution thus produced is brought into contact with a precipitating agent to form the base membrane, and the organic solvent is rinsed out after precipitation of the polymer mixture in flat or hollow-fibre form; and c) the base membrane produced in step b) is subjected to a surface modification in order to create a functional surface on it by carrying out at least one layer-by-layer [LbL] deposition on the surface of the base membrane so as to preserve the dialysis membrane, whereby at least one polymeric polycationic bonding agent is applied as the first layer on the surface of the base membrane and at least one polymeric polyanion is applied on the polycationic layer as the second layer; and whereby d) the polycationic bonding agent is selected from the group consisting of polyethylenimine [PEI] chitosan, polylysine, polyarginine and polyornithine, and mixtures of these; and a carboxylated polysaccharide or a sulfated polysaccharide is used as a polyanion, which is selected from the group consisting of: a dextran sulfate with a molecular mass ($M_w$) of 15 kDa to 300 MDa, a sulfated chitosan with a molecular mass ($M_w$) of 30 kDa to 750 kDa; a cellulose sulfate with a molecular mass ($M_w$) between 20 kDa and 1 MDa, preferably approx. 100 kDa; or mixtures of these; and whereby the pore-forming hydrophilic additive is selected from: polyvinylpyrrolidone [PVP], a short-chain glycol with 2 to 10 C atoms, triethylene glycol, propylene glycol, polyethylene glycol [PEG]/polyethylene oxide [PEO] and mixtures of these.

For the purposes of the present invention, the term "surface of the base membrane" is understood to include both the outer and the lumen surface.

A suitable precipitating agent for step b) in the above method is a mixture of the organic solvent and water with a solvent content of 5 to 85 weight %.

For production using the method according to aspects of the invention, the polyethylene glycol/polyethylene oxide can exhibit a molecular mass ($M_w$) of 600 Da to 500 kDa, in particular approx. 8 to 10 kDa and/or the PVP a molecular mass ($M_w$) of 1 kDa to 2.2 MDa.

Typically, the method according to aspects of the invention uses PEI as a bonding agent, whereby preference is given to a PEI with a molecular mass of 1 kDa-2 MDa, in particular approx. 750 kDa, or a C2 to C8-dialkanal cross-linked, in particular 1,5-pentanedial cross-linked, high-molecular PEI, preferably one which can be made from a PEI with a molecular mass of approx. 1.8 kDa by cross-linking with 1,5-pentanedial.

The polysaccharides used in the method according to aspects of the invention are preferably a dextran sulfate with a molecular mass ($M_w$) of 15 kDa to 1 MDa, in particular approx. 500 kDa and/or a sulfated chitosan with a molecular mass ($M_w$) of 30 kDa to 750 kDa; or mixtures of these.

In the method described, the pore-forming additive is selected from: a PVP with a molecular mass of approx. 1.1 MDa, glycerine, a PEG/PEO with a molecular mass of 600 Da to 500 kDa, in particular 8 to 10 kDa, or a 3-component mixture of these.

It is further preferred that the polymeric polycationic bonding agent, in particular PEI, is applied to the finished base membrane by spraying or by addition to the precipitating agent to the surface of the base membrane.

Both the polycationic bonding agent and the polyanionic functional layer can particularly preferably be applied by flushing into the lumen of a capillary membrane at a flushing station.

A further preferred embodiment of the method according to aspects of the invention is wherein the components of the casting or spinning solution are fully dissolved at 20 to 70° C. for 2 to 18 h and the homogeneous casting or spinning solution is evacuated at 100 to 800 mbar for 5 to 45 mins to remove air bubbles.

Another preferred embodiment of the method according to aspects of the invention is wherein the casting or spinning solution exhibits a viscosity of 0.2 to 5.0 Pa*s (@20° C.)

Another preferred embodiment of the method according to aspects of the invention is wherein pore-forming additive is selected from: a PVP with a molecular mass ($M_w$) of 1.1 kDa to 2.2 MDa, glycerine, a PEG/PEO with a molecular mass of 600 Da to 500 kDa ($M_w$), in particular approx. 8 kDa ($M_w$) or a 3-component mixture of these.

Another preferred embodiment of the method according to aspects of the invention is wherein the polymeric polycationic bonding agent, in particular PEI, is applied by spraying onto the finished base membrane or by addition to the precipitating agent onto the surface of the base membrane or by flushing onto the surface of the base membrane at a flushing station.

Another preferred embodiment of the method according to aspects of the invention is wherein the polymeric polycationic bonding agent, in particular PEI, is applied according to a ratio of 1 to 4000 µg/cm² of membrane surface.

Another preferred embodiment of the method according to aspects of the invention is wherein the polymeric polyanionic polysaccharide, in particular DEXS, is applied according to a ratio of 1 to 1500 µg/cm² of membrane surface.

Another preferred embodiment of the method according to aspects of the invention is wherein the polymeric polyanionic polysaccharide, in particular DEXS, is applied in a 0.01 to 1 M NaCl solution.

Another preferred embodiment of the method according to aspects of the invention is wherein the polymeric polyanionic polysaccharide, in particular DEXS, is applied by flushing onto the lumen surface of the base membrane at a flushing station, thereby selectively configuring the separation properties of the resulting composite membrane.

Another preferred embodiment of the method according to aspects of the invention is wherein the polymeric polycationic bonding agent, in particular PEI, and the polymeric polyanionic polysaccharide, in particular DEXS, are applied with a transmembrane pressure (TMP) of 10 to 250 mbar and a coating time of 2 to 900 s respectively.

BRIEF DESCRIPTION OF THE DRAWINGS

The invention is best understood from the following detailed description when read in connection with the accompanying drawings. Included in the drawings are the following figures.

DETAILED DESCRIPTION OF PREFERRED EMBODIMENTS

I. General Description of the Production of Base Membranes with Different Polymers.

casting or spinning solutions made of base membrane-polymer/additive/solvent were produced as follows: First of all, the selected additive and the desired polymer/polymer blend is slowly dissolved in N,N-dimethylacetamide [DMAc] and an appropriate amount of water (solution 1).

The following compounds were used as membrane polymers: polysulfone [PSU] ($M_n$ 16-22 kDa, $M_w$ 40-85 kDa), sulfonated polysulfone [SPSU] ($M_w$ 50-55 kDa, $M_n$ 27-32 kDa), polyethersulfone [PES] ($M_w$ 30-75 kDa, $M_n$ 16-22 kDa), sulfonated polyethersulfone [SPES] ($M_w$ 30-35 kDa, $M_n$ 18-22 kDa), polyphenylsulfone [PPSU] ($M_w$ 52-55 kDa, $M_n$ 22 kDa), sulfonated polyphenylsulfone [SPPSU] ($M_w$ 47-53 kDa, $M_n$ 17-21 kDa); and mixtures (blends) of these.

The modification of the polymers PSU and PES was realized with post-sulfonation. The polymer was dissolved in dichlormethane under inert gas (concentration 3 to 10 weight %). Chlorosulfonic acid was used as a reagent. 3 to 10 g of polymer (PSU or PES) was used. The amount of chlorosulfonic acid (0.1 to 20 ml) and the reaction time (addition within 5 to 45 minutes; then 1 to 5 hours reaction time) were varied so as to adjust the sulfonation degree. The reaction was carried out at room temperature. After this, the polymer solution was transferred to ice-cold water as a precipitation bath and the solid polymer was rinsed until a pH value of 6-7 was reached. Finally, the modified polymer was dried in a vacuum drying chamber at 40° C.

Sulfonated polyphenylsulfone [SPPSU] can be produced by copolymerization, according to the literature, e.g. Wang et al.: Macromol. Symp. 175, 387-395 (2001) and/or the dissertation by Jeffrey B. Mecham, Faculty of chemistry at the Virginia Polytechnic Institute and State University, Blacksburg, Va., USA, 23 Apr. 2001.

Here the monomers used were commercially available 4,4'-dihydroxybiphenyl (BP), 4,4'-dichlorodiphenyl sulfone (DCDPS) and disodium-3,3'-disulfonate-4,4"-dichlorodiphenyl sulfone (sDCDPS). All reactions were carried out in N-Methylpyrrolidone (NMP). The base used was potassium carbonate.

The following describes one way to produce sPPSU as an example:

In a 2 l HWS flask with stirrer, Dean-Stark apparatus, nitrogen inlet and temperature control, the following were suspended under nitrogen atmosphere in 1000 ml NMP: 258.37 g 4,4'-dichlorodiphenyl sulfone (DCDPS), 186.21 g 4,4'-dihydroxybiphenyl (BP), 49.12 g 3,3'-disodium disulfate-4,4'-dichlorodiphenyl sulfone and 146.5 g potassium carbonate (average particle size 50 μm). The mixture was stirred and heated to 190° C. The mixture was gassed with 20 l/h of nitrogen and kept at 190° C. for 6 h. After this, 500 ml NMP was added so as to cool the mixture. The mixture was cooled under nitrogen to below 60° C. After filtration, the mixture was precipitated in water containing 50 ml 2 m HCl. The precipitated product was extracted for 20 h at 85° C. with hot water and dried for 24 h under reduced pressure at 120° C.

The molecular weight distribution was determined with GPC using DMAc/LiBr as a solvent and PMMA samples with close molecular weight distribution as standards so as to calibrate the system.

As described above, the desired polymer/polymer blend was then slowly dissolved in N,N-dimethylacetamide [DMAc] and an appropriate amount of water (solution 1). This solution 1 was continuously stirred at 40° C., when polyethylene glycol with an $M_n$ of 10,000 Da was added. If PVP was used, stirring was carried out at 70° C., whereby a poly(vinylpyrrolidone) with a weight average molar mass $M_w$ of approx. 1.1 MDa was used. In order to achieve full dissolution of the polymer components, the mixtures were stirred for at least 3 to 12 h. If by this time no full dissolution had been achieved, stirring was continued for further hours.

The finished homogeneous casting or spinning solution was degassed at 100 mbar for 15 mins in order to remove air bubbles.

Unless stated otherwise, all percentages are shown in weight % and the term "molar mass", unless stated otherwise, refers to the weight average molar mass $M_w$ or the number average molar mass $M_n$, both of which can be measured with gel permeation chromatography with the relevant molecular mass standards. The reason for this is that the weight average molar mass is of greater importance for the property correlations of plastics in practice than the number and viscosity averages (see Saechtling, Kunststoffttaschenbuch, 31st edition, Carl Hanser Verlag, Munich 2013).

TABLE 1

Parameters for the characterization of molar masses with GPC

|  | PEI | DEXS | PSU, PES, PPSU, SPSU, SPES, SPPSU |
|---|---|---|---|
| Column | NOVEMA 10000A, 10 μm (PSS) | SUPREMA 10000A, 10 μm (PSS) | GRAM pre-column + 2x GRAM, 10 μm (PSS) |
| Eluent | 0.1M NaCl 0.25% HCOOH 0.01% NaN3 | 0.4M NaCl 0.1M NaNO3 0.01% NaN3 | DMAc 0.01M LiBr |
| Volumetric flow rate [ml/mins] |  | 1 |  |
| Concentration Polymer [g/L] | 2.5 | 1.0 | 4.0 |
| Detector | RI | RI | ETA 2010 RI/VIS |
| Standard | PVP 900 Da-1 MDa | Pullulan 180 Da-780 kDa | PMMA 0.1-1000 kg/mol |

To produce flat membranes, these are made according to the non-solvent-induced phase separation method [NIPS]. The polymer solution is extruded in a Coatmaster 509 MC (Erichsen GmbH & CO. KG, Hemer) on a glass plate at a constant squeegee speed of 25 mm/s with a stainless steel squeegee with a gap height of 200 μm to form the protomembrane in a controlled atmosphere with a relative air humidity of <30% at room temperature. The temperature of membrane production—casting solution, glass plate, stainless steel squeegee, precipitation bath—was varied from room temperature to 60° C.

The cast film thereby obtained is subsequently immersed for 5 mins in a precipitation bath, which contains as the precipitating agent 500 ml of a mixture of 50 vol. % DMAc/50 vol. % $H_2O$.

After precipitation, the membrane is transferred to water, whereby the water is changed three times, after 20 mins in each case. For so-called wet variants (see Table 2) the membranes are cut to the final size and samples are kept at room temperature in an aqueous solution of 10 mM sodium azide for characterization or LbL modification. In the case of dry variants, the membranes are dried for 6 mins at 100° C. after rinsing and prior to further stages.

In order to make hollow-fibre membranes, the finished polymer spinning solution described above is introduced into the annular gap of a hollow-filament nozzle which is maintained at a temperature of approx. 60° C. At the same time, for the formation of lumen and induction of the precipitation process, a mixture of 50 vol. % DMAc/50 vol. % H$_2$O is fed through the jet needle of the hollow-filament nozzle. The fully-formed hollow-fibre membrane was guided through a channel in which the temperature was 50° C. and the relative air humidity was 90%, precipitated in warm precipitating agent which was at a temperature of approx. 70° C. (50 vol. % DMAc/50 vol. % H$_2$O) fixed and subsequently rinsed and preserved as was the case for the flat membranes.

After drying, hollow-fibre membranes had formed with a lumen diameter of 200 μm and a wall thickness of 30 μm.

I.1. Modification of the Base Membrane: Layer-by-layer Deposition

The surface modification of the flat membranes produced according to the above description was carried out with an Amicon® ultrafiltration measuring cell or in a cell replicated in analogue form and dimensions. First of all, a solution of a commercially available polyethylenimine (750 kDa) was filtered in a ratio of 3.7 mg/cm$^2$ of membrane surface through the membrane for 5 mins at 50 mbar in order to apply an initial layer of a polymeric cationic bonding agent onto the membrane surface. Then the membrane surface was rinsed with water and water was subsequently filtered through the membrane for 5 mins at 50 mbar. After this, a 1 M NaCl solution was filtered for 2 mins at 50 mbar through the membrane. The membrane was then coated with filtration with a dextran sulfate solution (DEXS solution, 500 kDa in 1 M NaCl) in a ratio of 1.5 mg/cm$^2$ of membrane surface for 5 mins at 50 mbar to create the second layer containing the polymeric polyanion. The membrane was then rinsed as described above so as to remove surplus dextran sulfate.

If necessary the LbL coatings described above can be repeated several times so as to finally obtain a functional layer with the desired properties.

For the LbL coating of the hollow-fibre membranes produced as part of the present invention, the hollow fibres were first introduced to a dialysis module, then they were loosely packed, and subsequently the LbL coating was carried out as described for the flat membranes.

I.2. Permeability and Retention Studies

I.2.1. Characterization of the Base Membranes

The filtration experiments were carried out in the so-called dead-end configuration model using an Amicon® ultrafiltration measuring cell or an self-constructed cell with a stirring device. In all experiments, a PP fleece was placed under the membranes to be tested so as to prevent the cell floor from mechanically altering the membrane.

First the membranes were subjected to a compaction. This is an alternating pressure load whose effects lead to changes in the membrane structure, resulting in a loss of water permeability. The membranes were first compacted for at least 30 mins with filtrations of ultrapure water at 0.5 bar until a quasi-constant flow was achieved. Then the pressure was relieved for 10 mins and the water permeability was measured for a pressure difference of 0.1 to 0.5 bar. The existing water permeability Lp, expressed in L h$^{-1}$ m$^{-2}$ bar$^{-1}$, was standardized to a temperature of 20° C.

The loss in permeability as a result of compaction was determined from these experiments based on the following equation 1:

$$Lp_{compaction\ loss}(\%) = \left(1 - \frac{Lp \text{ after compaction @ } 0.5 \text{ bar}}{Lp \text{ before compaction @ } 0.5 \text{ bar}}\right) \times 100 \quad (1)$$

The membranes produced were tested with bovine serum albumin (BSA, Probumin, Millipore) with ultrafiltration. First of all, the membranes for testing were conditioned for two minutes by filtration of a phosphate buffer solution (8 g/L NaCl, 1,182 g/L Na$_2$HPO$_4$.2H$_2$O, 0.9 g/L KH$_2$PO$_4$) at 50 mbar. After this, a known volume of a BSA solution was filtered through the membrane as a feed with a concentration of 30 g/L BSA in phosphate buffer—in a ratio of 2.4 ml/cm$^2$ of the membrane at 30 mbar, and permeate and retentate samples were collected in a ratio of 1:5. The concentrations in the feed solution, retentate and permeate were measured at 278.5-279.5 nm (after the relevant calibration). The sieving coefficient S for BSA was calculated according to equation 2:

$$S = \frac{2 \times C_{permeate}}{C_{feed} + C_{retentate}} \quad (2)$$

$C_{permeate}$, $C_{feed}$ and $C_{retentate}$ are the relevant BSA concentrations in the permeate, feed and retentate.

After this, the membranes were carefully rinsed and stirred for 15 minutes with ultrapure water in the Amicon® cell so as to remove the weakly bound fouling layer. Then the permeability was measured once again and fouling resistance $R_f$ was calculated as follows:

$$R_f = \frac{Lp^*}{Lp} \quad (3)$$

whereby Lp and Lp* are the permeabilities before and after BSA filtration.

For the purposes of the present application, the term "molecular weight cut-off" (MWCO) is deemed to be the molecular mass which is 90% retained by a membrane. The unit is Da.

Determining the molecular weight cut-off was carried out with a dextran wide band mixture (feed) with a concentration of 1.1 g/l (mass distribution/litre: 0.20 g 1 kDa, 0.25 g 4 kDa, 0.15 g 8 kDa, 0.07 g 15 kDa, 0.10 g 35 kDa, 0.15 g 70 kDa, 0.05 g 110 kDa, 0.13 g 250 kDa) in water with 0.01% sodium azide. The feed was filtered through the membrane in a ratio of o2.4 ml/cm$^2$ of the membrane at 30 mbar @ room temperature, and permeate and retentate samples were collected in a ratio of 1:5. The concentrations in the feed solution, retentate and permeate were then analyzed with gel permeation chromatography (PL-GPC 50 Plus, Varian). The column used was a PROTEEMA 300A (PSS), PL aquagel-OH Mixed 8 μm (Agilent) and 0.01% NaN$_3$ in H$_2$O with a flow rate of 1 ml/min was used an eluent. 100 μl of each sample was injected. The analysis was carried out based on a calibration using the polysaccharide standard.

The sieving coefficient for each molar mass is calculated from the data with software:

$$S = \frac{2 \cdot c_{permeate}}{c_{feed} + c_{retentate}} \quad (4)$$

The sieving curve is obtained for each membrane by showing the sieving coefficient in relation to molar mass (logarithmic application). The sieving curve is then used to determine the cut-off for a sieving coefficient of 0.1. The term "molecular weight cut-off" (MWCO) is deemed to be the molecular mass which is 90% retained by the membrane. The unit is Dalton [Da].

I.2.2. Characterization of the LbL-modified Membranes

In order to characterize the LbL-modified membranes, the measurements were carried out in the same way as described above for the base membranes. First of all the unmodified membranes were compacted and permeability was measured (at a pressure difference of 0.1 to 0.5 bar). Then the LbL coating was carried out as described in Section I.2. After the LbL coating, the new permeability was measured and the permeability loss due to LbL deposition $Lp_{LbL\ loss}$ was calculated according to equation 4:

$$Lp_{LbLloss}(\%) = \left(1 - \frac{LpafterLbLdeposition}{LpbeforeLbLdeposition}\right) \times 100 \quad (5)$$

The new membrane capacity was also measured based on BSA retention using the same method as for the base membranes. Finally the membranes were once again carefully rinsed and stirred for 15 minutes using ultrapure water and then again rinsed for 5 mins at a pressure of 0.1 bar. After this, the permeability was once again measured and the MWCO and fouling resistance $R_{f-LbL}$ were calculated.

I.3. Contact Angle Measurements

The contact angle in "°" was determined using an optical contact angle measuring device. The measurements were carried out using a static captive bubble method (air bubble volume: 5 μl). For each sample, at least five measurements were carried out in different positions and then the average was calculated.

I.4. Zeta Potential Measurements

In order to determine the surface charge of the lumen surface of the membranes produced, the zeta potential was measured using the commercial electrokinetic analyzer SurPASS (Anton Paar). Prior to each experiment, the membranes to be measured were equilibrated for one hour in an electrolyte solution of 1 mM KCl. The experiments were then carried out at room temperature from a pH value of 3, set with an HCl solution, up to final pH value of 11.5, gradually increased by the addition of a KOH solution.

I.5. Rheological Measurements

The viscosity of the casting and spinning solutions produced was measured using a rheometer fitted with a Peltier element for the purpose of temperature control. The experiments were carried out at a constant shear rate (125 1/s) and at a temperature difference (between 20 and 60° C.) using a measurement system with a cone plate (CP25-2 TG).

II. Results

The composition of the casting solutions to produce flat membranes as model membranes and the production temperature are shown in Table 2.

In the table, PSU is polysulfone, while SPPSU1, SPPSU2, SPPSU10, SPPSU14 indicate the respectively specified sulfonation degree of the sulfated polyphenylsulfones used in weight %; according to this the following sulfonation degrees apply to the above-specified sulfonated polyphenylsulfones: 1.1; 3.6 and 14.1 weight %.

For the sulfonated polysulfonethers used, the same applies to them in terms of their respective sulfonation degree in the same way as for the nomenclature set out above for the sulfonated polysulfones, namely SPES3, SPES2 and SPES4. These sulfonated polyethersulfones thus exhibit a sulfonation degree of 1.1; 3.6 and 14.1 weight %.

Five different sets of casting solutions were selected for the experiments:

Set 1: 15% polymer content in the casting solution using different proportions of SPPSU and PVP as an additive.

Set 2: 17% polymer content in the casting solution using different proportions of SPPSU and PVP as an additive.

Set 3: 16% polymer content in the casting solution using different proportions of SPPSU and PEG/PEO as an additive.

Set 4: 15% polymer content in the casting solution using different proportions of SPES and PVP as an additive.

A summary of the experimental data obtained for the membranes tested is shown in Table 3.

TABLE 2

Compositions for the solutions and casting conditions used for membrane production

| Polymer solutions | Set 1<br>S0-PVP-B | Set 1<br>S1-PVP-B | Set 1<br>S2-PVP-B | Set 1<br>S10-PVP-B | Set 1<br>S14-PVP-B | Set 2<br>S2-PVP-D | Set 2<br>S10-PVP-5D |
|---|---|---|---|---|---|---|---|
| PSU/SPPSU* | 15/0 | 13.5/1.5 | 13.5/1.5 | 13.5/1.5 | 13.5/1.5 | 15.3/1.7 | 16.2/0.8 |
| PVP/DMAc/H$_2$0 | 3.7/80.8/0.5 | 3.7/80.8/0.5 | 3.7/80.8/0.5 | 3.7/80.8/0.5 | 3.7/80.8/0.5 | 3.7/78.8/0.5 | 3.7/78.8/0.5 |
| Production temperature (° C.) | 60 | 60 | 60 | 60 | 60 | 60 | 60 |

| Polymer solutions | Set 3<br>S2-PEG-A | Set 3<br>S2-PEG-A-25 | Set 3<br>S10-PEG-A | Set 3<br>S14-PEG-A | Set3<br>P25 |
|---|---|---|---|---|---|
| PSU/SPPSU* | 14.4/1.6 | 14.4/1.6 | 14.4/1.6 | 14.4/1.6 | |
| PEG/DMAc | 5/79 | 5/79 | 5/79 | 5/79 | |

TABLE 2-continued

Compositions for the solutions and casting conditions used for membrane production

| | | | | | |
|---|---|---|---|---|---|
| PSU/PEG/DMAc | | | | | 16/5/79 |
| Production temperature (° C.) | 40 | 25 | 40 | 40 | 23 ± 3 |

| Polymer solutions | Set 4<br>SPES2-PVP-B | Set 4<br>SPES3-PVP-B | Set 4<br>SPES4-PVP-B | Set 5<br>P29 |
|---|---|---|---|---|
| PSU/SPES | 13.5/1.5 | 13.5/1.5 | 13.5/1.5 | |
| PVP/DMAc/H$_2$0 | 3.7/80.8/0.5 | 3.7/80.8/0.5 | 3.7/80.8/0.5 | |
| PPSU/PEG/DMAc | | | | 14.3/5.1/80.6 |
| Production temperature (° C.) | 60 | 60 | 60 | 23 ± 3 |

*The sulfonated polymers used are contained in the names of the polymer solution; S1, S2, S10 and S14 correspond to SPPSU1, SPPSU2, SPPSU10, SPPSU14 respectively.

TABLE 3

Summary of the experimental data of the membranes tested

| Polymer solution** | S0-PVP-B | S1-PVP-B | S2-PVP-B | S10-PVP-B | S14-PVP-B |
|---|---|---|---|---|---|
| Membrane state | wet | wet | wet | wet | wet |
| Lp before compaction @0.5 bar (L h$^{-1}$m$^{-2}$bar$^{-1}$) | 674 ± 78[6] | 746 ± 21[3] | 741 ± 121[7] | 1432 ± 137[5] | 1720 ± 446[8] |
| Lp after compaction @0.5 bar (L h$^{-1}$m$^{-2}$bar$^{-1}$) | 578 ± 31[6] | 709 ± 16[3] | 675 ± 122[7] | 1376 ± 161[5] | 1505 ± 482[8] |
| Lp compaction loss (%) | 13 ± 10[6] | 2 ± 2[3] | 9 ± 5[7] | 4 ± 2[5] | 14 ± 8[8] |
| Lp (L h$^{-1}$m$^{-2}$bar$^{-1}$) | 509 ± 55[6] | 652 ± 16[3] | 597 ± 92[7] | 1231 ± 204[5] | 1292 ± 412[8] |
| Lp BSA (L h$^{-1}$m$^{-2}$bar$^{-1}$) | 105 ± 9[3] | 138 ± 8[3] | 83 | 207 ± 26[3] | 278 ± 76[4] |
| Lp after BSA (L h$^{-1}$m$^{-2}$bar$^{-1}$) | 239 ± 37[3] | 277 ± 37[3] | 268 | 274 ± 20[3] | 349 ± 54[4] |
| Fouling resistance R$_f$ (—) | 0.44 ± 0.03[3] | 0.42 ± 0.05[3] | 0.61 | 0.24 ± 0.03[3] | 0.36 ± 0.07[4] |
| Sieving coefficient | 0.063 ± 0.065[3] | 0.054 ± 0.017[3] | 0.020 ± 0.002[3] | 0.085 ± 0.044[3] | 0.154 ± 0.086[4] |
| Layer by layer | | | | | |
| Lp LbL @0.5 bar (L h$^{-1}$m$^{-2}$bar$^{-1}$) | 433 ± 25[3] | — | 432 ± 49[3] | 693 [2] | 546 [2] |
| Lp LbL (L h$^{-1}$m$^{-2}$bar$^{-1}$) | 408 ± 22[3] | — | 406 ± 46[3] | 709 [2] | 514 [2] |
| Lp loss after LbL (%) | 15 ± 9[3] | — | 39 ± 4[3] | 45 [2] | 62 [2] |
| Lp BSA (L h$^{-1}$m$^{-2}$bar$^{-1}$) | 128 ± 23[3] | — | 99 ± 7[3] | 153 [2] | 120 [2] |
| Lp after BSA (L h$^{-1}$m$^{-2}$bar$^{-1}$) | 174 ± 26[3] | — | 164 ± 9[3] | 319 [2] | 255 [2] |
| Fouling resistance R$_{f-LbL}$ (—) | 0.43 ± 0.05[3] | — | 0.41 ± 0.04[3] | 0.45 [2] | 0.50 [2] |
| Sieving coefficient | 0.005 ± 0.002[3] | — | 0.005 ± 0.002[3] | 0.023 [2] | 0.017 [2] |
| Characterization | | | | | |
| Contact angle (°) | 47 ± 1 | 34 ± 2 | 39 ± 1 | 38 ± 3 | 41 ± 4 |
| Viscosity (Pa · s, 20° C.) | 3.4 | 3.4 | 3 | 2.7 | 2.3 |

**The sulfonated polymers used are contained in the names of the polymer solution; S1, S2, S10 and S14 correspond to SPPSU1, SPPSU2, SPPSU10, SPPSU14 respectively.

| Polymer solution | SPES3-PVP-B | SPES2-PVP-B | SPES4-PVP-B | S2-PVP-D | S10-PVP-5D |
|---|---|---|---|---|---|
| Membrane state | wet | wet | wet | Wet | wet |
| Lp before compaction @0.5 bar (L h$^{-1}$m$^{-2}$bar$^{-1}$) | 713 ± 126[5] | 744 ± 49[4] | 1335 ± 256[3] | 631 ± 81[7] | 931 ± 214[5] |
| Lp after compaction @0.5 bar (L h$^{-1}$m$^{-2}$bar$^{-1}$) | 625 ± 125[5] | 659 ± 66[4] | 1292 ± 228[3] | 564 ± 76[7] | 891 ± 202[5] |
| Lp compaction loss (%) | 13 ± 5[5] | 11 ± 6[4] | 3 ± 2[3] | 10 ± 7[7] | 4 ± 1[5] |
| Lp (L h$^{-1}$m$^{-2}$bar$^{-1}$) | 593 ± 104[5] | 630 ± 45[4] | 1206 ± 176[3] | 533 ± 97[7] | 774 ± 159[5] |
| Lp BSA (L h$^{-1}$m$^{-2}$bar$^{-1}$) | 117 ± 21[3] | 154 ± 30[3] | 208 | 154 ± 13[4] | 397 ± 97[3] |
| Lp after BSA (L h$^{-1}$m$^{-2}$bar$^{-1}$) | 243 ± 16[3] | 339 ± 30[3] | 247 | 193 ± 17[4] | 254 ± 34[3] |
| Fouling resistance R$_f$ (—) | 0.48 ± 0.08[3] | 0.52 ± 0.06[3] | 0.21 | 0.32 ± 0.02[4] | 0.32 ± 0.04[3] |
| Sieving coefficient | 0.146 ± 0.071[3] | 0.360 ± 0.197[3] | 0.893 | 0.067 ± 0.056[4] | 0.063 ± 0.032[3] |
| Layer by layer | | | | | |
| Lp LbL @0.5 bar (L h$^{-1}$m$^{-2}$bar$^{-1}$) | 520 [2] | 455 | 768 [2] | 287 ± 74[3] | 487 [2] |
| Lp LbL (L h$^{-1}$m$^{-2}$bar$^{-1}$) | 491 [2] | 463 | 739 [2] | 266 ± 72[3] | 457 [2] |
| LP loss after LbL (%) | 30 [2] | 16 | 38 [2] | 39 ± 13[3] | 35 [2] |
| Lp BSA (L h$^{-1}$m$^{-2}$bar$^{-1}$) | 124 [2] | 88 | 233 [2] | 103 ± 13[3] | 105 [2] |

TABLE 3-continued

Summary of the experimental data of the membranes tested

| | | | | | |
|---|---|---|---|---|---|
| Lp after BSA (L h$^{-1}$m$^{-2}$bar$^{-1}$) | 183 [2] | 242 | 307 [2] | 124 ± 18[3] | 166 [2] |
| Fouling resistance R$_{f-LbL}$ (—) | 0.37 [2] | 0.52 | 0.41[2] | 0.49 ± 0.08[3] | 0.36 [2] |
| Sieving coefficient | 0.030 [2] | 0.047 | 0.219 [2] | 0.002 [2] | 0.002 [2] |

Characterization

| | | | | | |
|---|---|---|---|---|---|
| Contact angle (°) | 35 ± 1 | 36 ± 3 | 44 ± 6 | 39 ± 5 | 44 ± 6 |
| Viscosity (Pa · s, 20° C.) | 2.3 | 2.6 | 2.2 | 4.4 | 4.2 |

| Polymer solution | S2-PEG-A | S10-PEG-A | S14-PEG-A | S2-PEG-A-25 |
|---|---|---|---|---|
| Membrane state | wet | wet | Wet | wet |
| Lp before compaction @0.5 bar (L h$^{-1}$m$^{-2}$bar$^{-1}$) | 2723 ± 335[6] | 3063 ± 219[6] | 3625 ± 340[3] | 2670 |
| Lp after compaction @0.5 bar (L h$^{-1}$m$^{-2}$bar$^{-1}$) | 2507 ± 273[6] | 2824 ± 159[6] | 2888 ± 318[3] | 2316 |
| Lp compaction loss (%) | 8 ± 4[6] | 8 ± 4[6] | 20 ± 9[3] | 13 |
| Lp (L h$^{-1}$m$^{-2}$bar$^{-1}$) | 2266 ± 286[6] | 2272 ± 114[6] | 2651 ± 260[3] | 2126 |
| Lp BSA (L h$^{-1}$m$^{-2}$bar$^{-1}$) | 535 ± 64[3] | 478 ± 22[3] | 720 | — |
| Lp after BSA (L h$^{-1}$m$^{-2}$bar$^{-1}$) | 805 ± 132[3] | 921 ± 68[3] | 1181 | — |
| Fouling resistance R$_f$ (—) | 0.38 ± 0.02[3] | 0.42 ± 0.03[3] | 0.49 | — |
| Sieving coefficient | 0.193 ± 0.055[3] | 0.293 ± 0.036[3] | 0.647 | — |

Layer by layer

| | | | | |
|---|---|---|---|---|
| Lp LbL @0.5 bar (L h$^{-1}$m$^{-2}$bar$^{-1}$) | 1142 ± 166[3] | 853 ± 36[3] | 1270 [2] | 1042 |
| Lp LbL (L h$^{-1}$m$^{-2}$bar$^{-1}$) | 1102 ± 144[3] | 793 ± 26[3] | 1220 [2] | 974 |
| LP loss after LbL (%) | 54 ± 5[3] | 66 ± 1[3] | 56 [2] | 54 |
| Lp BSA (L h$^{-1}$m$^{-2}$bar$^{-1}$) | 161 ± 39[3] | 283 ± 15[3] | 215 [2] | 186 |
| Lp after BSA (L h$^{-1}$m$^{-2}$bar$^{-1}$) | 448 | 384 ± 28[3] | 526 | — |
| Fouling resistance R$_{f-LbL}$ (—) | 0.34 | 0.48 ± 0.02[3] | 0.42 | — |
| Sieving coefficient | 0.012 ± 0.004[3] | 0.006 ± 0.003[3] | 0.032 [2] | 0.007 |

Characterization

| | | | | |
|---|---|---|---|---|
| Contact angle (°) | — | — | — | — |
| Viscosity (Pa · s, 20° C.) | 0.8 | 0.7 | 0.7 | 0.8 |

| Polymer solution | P25* | P29* | P29_limA** | P29_limB** | P29 limB** |
|---|---|---|---|---|---|
| Membrane state | wet | Dry | dry | Dry | wet |
| Lp before compaction @0.5 bar (L h$^{-1}$m$^{-2}$bar$^{-1}$) | 2423 ± 325[18] | 1208 ± 252[27] | 1208 ± 252[27] | 1208 ± 252[27] | 3638 ± 1241[4] |
| Lp after compaction @0.5 bar (L h$^{-1}$m$^{-2}$bar$^{-1}$) | 1899 ± 320[18] | 690 ± 284[27] | 690 ± 284[27] | 690 ± 284[27] | 1985 ± 298[4] |
| Lp compaction loss (%) | 21 ± 10[18] | 44 ± 18[27] | 44 ± 18[27] | 44 ± 18[27] | 56 ± 29[4] |
| Lp (L h$^{-1}$m$^{-2}$bar$^{-1}$) | — | — | — | — | 356[1] |
| Lp BSA (L h$^{-1}$m$^{-2}$bar$^{-1}$) | — | — | — | — | — |
| Lp after BSA (L h$^{-1}$m$^{-2}$bar$^{-1}$) | — | 300 ± 80[4] | 300 ± 80[4] | 300 ± 80[4] | 1103[1] |
| Fouling resistance R$_f$ (—) | — | 0.69 ± 0.09[4] | 0.69 ± 0.09[4] | 0.69 ± 0.09[4] | 0.48[1] |
| Sieving coefficient | 0.0640[2] | 0.247 ± 0.078[5] | 0.247 ± 0.078[5] | 0.247 ± 0.078[5] | 0.3542[1] |
| MWCO (kDa) | 113 ± 6[8] | 97 ± 3[6,2] | 97 ± 3[6,2] | 97 ± 3[6,2] | 122[1] |

Layer by layer

| | | | | | |
|---|---|---|---|---|---|
| Lp LbL (L h$^{-1}$m$^{-2}$bar$^{-1}$) | 720 ± 193[11] | 65 ± 22[3] | 228 ± 39[3] | 138 ± 82[9] | 456[2] |
| LP loss after LbL (%) | 58 ± 12 | 84 ± 11[3] | 64 ± 15[3] | 79 ± 15[9] | 71[2] |
| Lp BSA (L h$^{-1}$m$^{-2}$bar$^{-1}$) | 167 ± 32[7] | — | 60[1] | 36 ± 16[3] | 113[2] |
| Lp after BSA (L h$^{-1}$m$^{-2}$bar$^{-1}$) | 428 ± 117[7] | — | 147[1] | 107 ± 41[3] | 118[2] |
| Fouling resistance R$_{f-LbL}$ (—) | — | — | 0.65[1] | 0.56 ± 0.12[3] | 0.26[2] |
| Sieving coefficient | 0.0013 ± 0.0005[7] | — | 0.0083[1] | 0.0045 ± 0.0009[3] | 0.01215[2] |
| MWCO (kDa) | 34 ± 2[5] | 29[1] | 50[2] | — | — |

Figure 1:
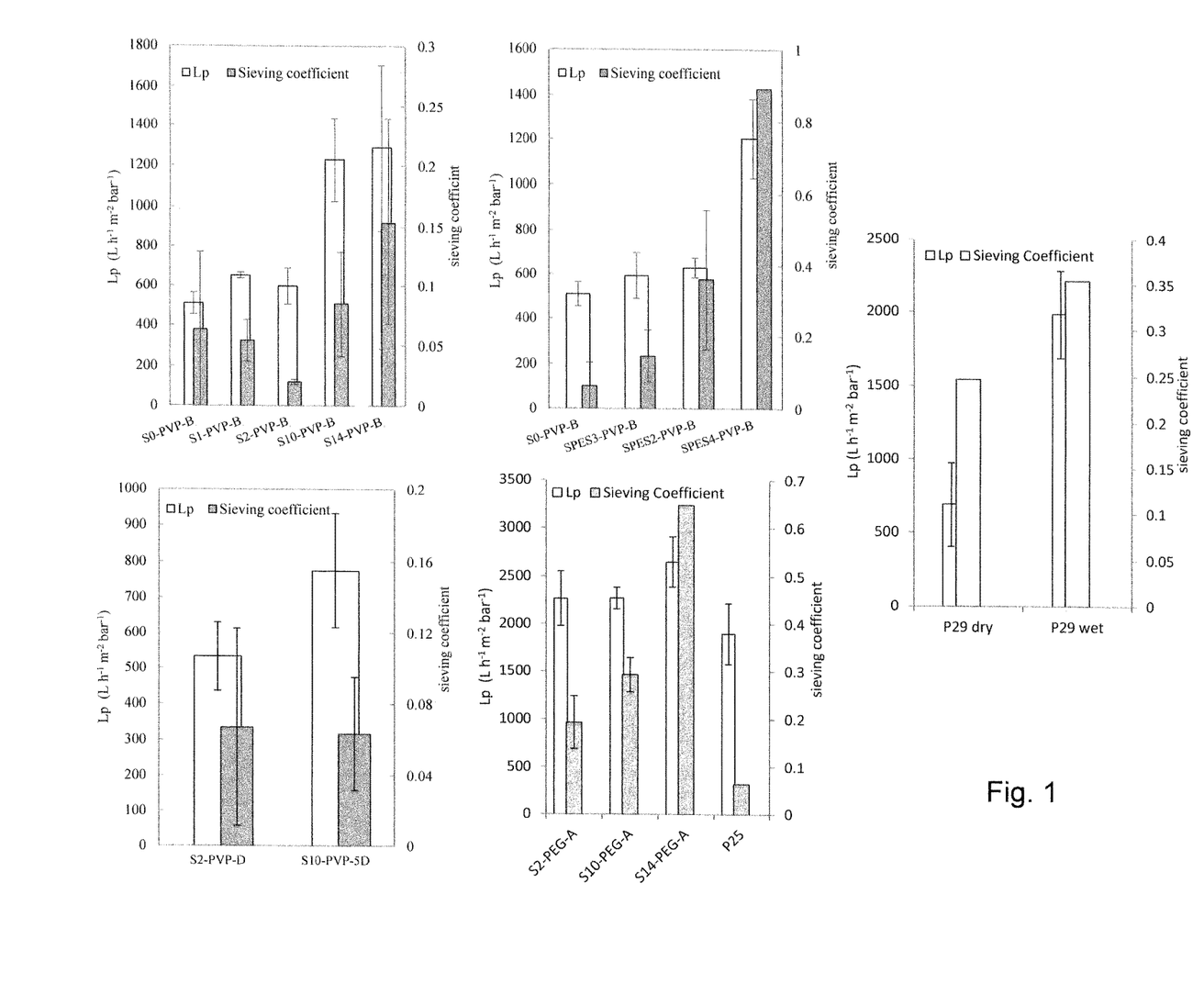
FIG. 1 is a series of graphs depicting the water permeability and sieving coefficients of five different sets of base membranes prior to their LbL modification.

*LbL modification was carried out according to I.1
**LbL modification with limited quantities of polyelectrolyte: 112 µg/cm² PEI (750 kDa, 50 mbar, 5 mins), 21 µg/cm² DEXS (500 kDa, 50 mbar, 5 mins) for limA; 3.7 mg/cm² PEI (750 kDa, 50 mbar, 5 mins), 21 µg/cm² DEXS (500 kDa, 50 mbar, 5 mins) for limB In order to illustrate the properties of the membranes according to aspects of the invention more clearly, FIG. 1 shows the water permeabilities and sieving coefficients of five different membrane types measured prior to modification (see Table 2 and 3). The hydraulic permeabilities of the base membranes are between 10 and 5,000 L/bar*h*m$^2$ and exhibit a sieving coefficient (@22±2° C.) for BSA in the range of 0.9 to 0.001 and an MWCO of 3 kDa to 250 kDa. In the case of membranes with moderate flux, which correspond to the membranes with PVP as the additive, the results show clearly that the use of sulfonated polymers leads to a drastic increase in water permeability, which is presumably mainly due to a higher membrane hydrophily of such membranes.

For the high-flux membranes—corresponding to the membranes with PEG/PEO as the additive—the effect is less marked, however. Nonetheless, high permeabilities are obtained in all cases at the expense of size retention properties. An assumed increase in pore size is probably the reason for this. Low viscosities are obtained for those casting solutions which were produced using polymers with a higher sulfonation degree. This induces a change in membrane formation during the phase inversion process.

Figure 2:
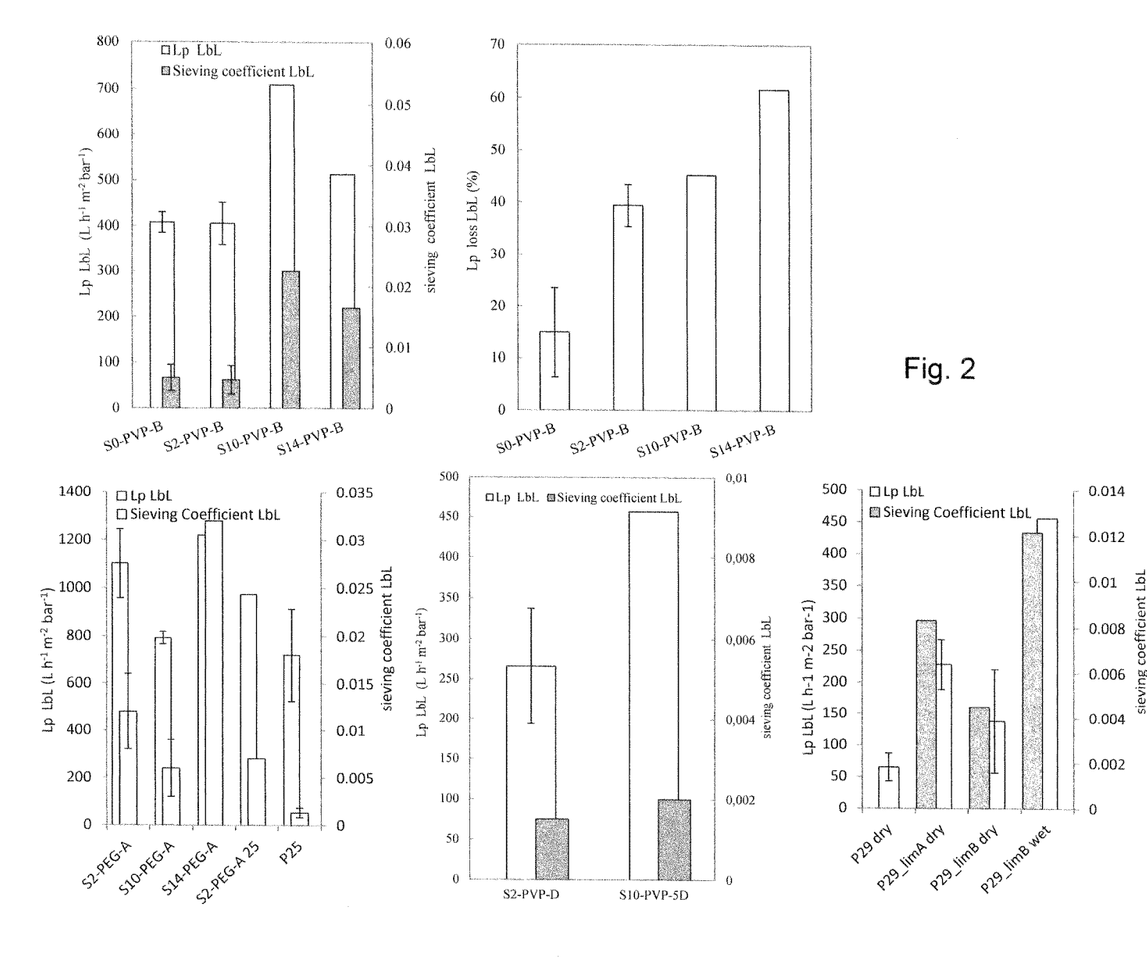
FIG. 2 is a series of graphs depicting the effect of LbL deposition on water permeability and the sieving coefficient for BSA at 22±2° C. for the polymers of the five different sets of membranes.

FIG. 2 shows the effect of LbL deposition on water permeability and the BSA sieving coefficient for four different sets of membranes, as well as the induced reduction in permeability due to LbL deposition.

After LbL coating with the polyelectrolytes, a drop in permeability is observed of up to 84%. In particular for set 1 with PVP as the additive, a direct correlation is observed between the sulfonation degree of the polymer and the permeability; the use of a sulfonated polymer with a higher sulfonation degree in the mixture solution results in a greater reduction in permeability through the coating.

Without being bound to this, it is possible that on the one hand the presence of a higher charge density on the membrane surface results in better bonding of the polyelectrolytes during deposition. On the other hand, the same quantity of polyelectrolytes could have been deposited and the greater reduction in permeability could have been caused by the existence of larger pores at the beginning of the LbL process, whereby the pores could have been narrowed or blocked during the deposition of the polyelectrolytes as a result of modification.

Furthermore, FIG. 2 shows that high permeabilities and low sieving coefficients are obtained for the membranes produced with PEG/PEO as the additive after modification. S2-PEG-A, S2-PEG-A25, S10-PEG-A and P25 show respective water permeabilities of 1102±144 L*bar*h−1*m−2, 974 L*bar*h−1*m−2, 793±26 L*bar*h−1*m−2, 720±193 L*bar*h−1*m−2 and sieving coefficients for BSA at 22±2° C. of 0.012±0.004, 0.007, 0.006±0.003 and 0.0013±0.0005.

Membranes modified according to aspects of the invention from set 2, consisting of a polymer solution containing 17% polymer and PVP as the additive show a high performance. Water permeabilities were achieved of 266±72 L*bar*h−1*m−2 and 457 L*bar*h−1*m−2, and BSA sieving coefficients were obtained for S2-PVP-D and S10-PVP-5D of 0.002 in each case Composite membranes from set 4, produced from a polymer solution with 14.3% polymer and PEG as the additive, show water permeabilities of 65±22 to 456 L*bar*h−1*m−2 and BSA sieving coefficients of 0.0083 to 0.01215, depending on the coating quantity and the conditions at modification.

The result obtained was a wide range of membranes with a medium to high level of water permeability. Furthermore, the results show that the LbL coating has the dominating influence on water permeability and the sieving coefficient for BSA, resulting in the fact that the membranes obtained with LbL coating are suitable for dialysis application.

In particular, in the context of the present invention it was possible to achieve control over the membrane surface charge by adjusting the content and sulfonation degree of the polymer used.

Using the present invention, therefore, it is possible to produce membranes suitable for purifying blood (or dialysis) which exhibit a water permeability in the range of 10 to 2000 L*bar*h−1*m−2 and a sieving coefficient @22±2° C. for BSA in the range of 0.0001 to 0.5.

Figure 3:
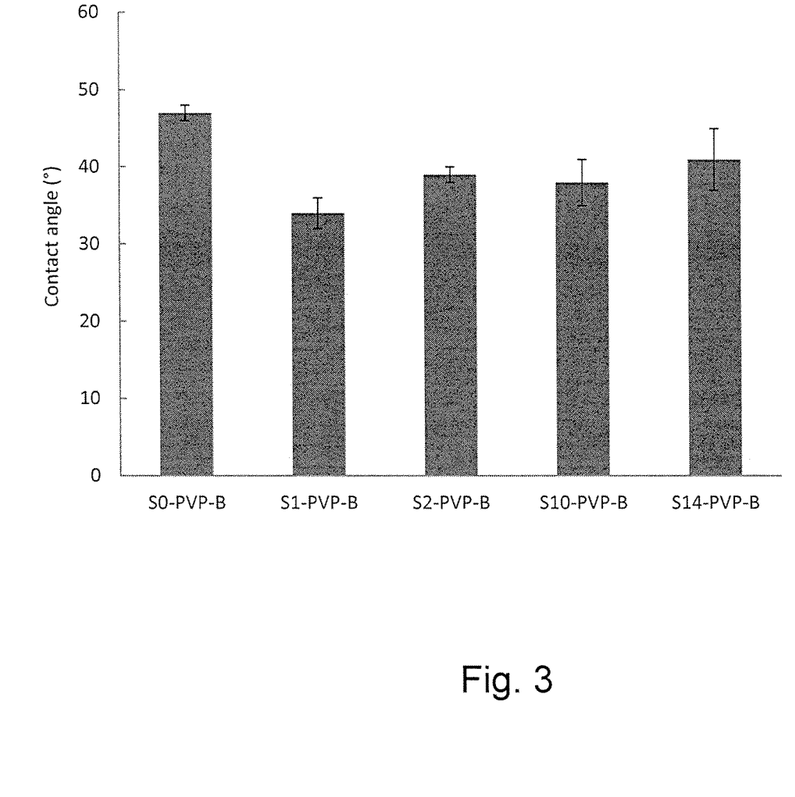
FIG. 3 is a graph depicting the contact angle of non-modified membranes of set 1 as a measurement of wettability.

A supplementary analysis relating to the hydrophily of the membranes (in particular set 1) is shown in FIG. 3: this shows contact angle measurements on a PSU/PVP base membrane (S0-PVP-B) and on membranes made from sulfonated polymer blends (mixtures). As shown in FIG. 3, the introduction of sulfonated groups to a polysulfone also results in a reduction of the contact angle and therefore to improved wettability of the membranes.

Figure 4:
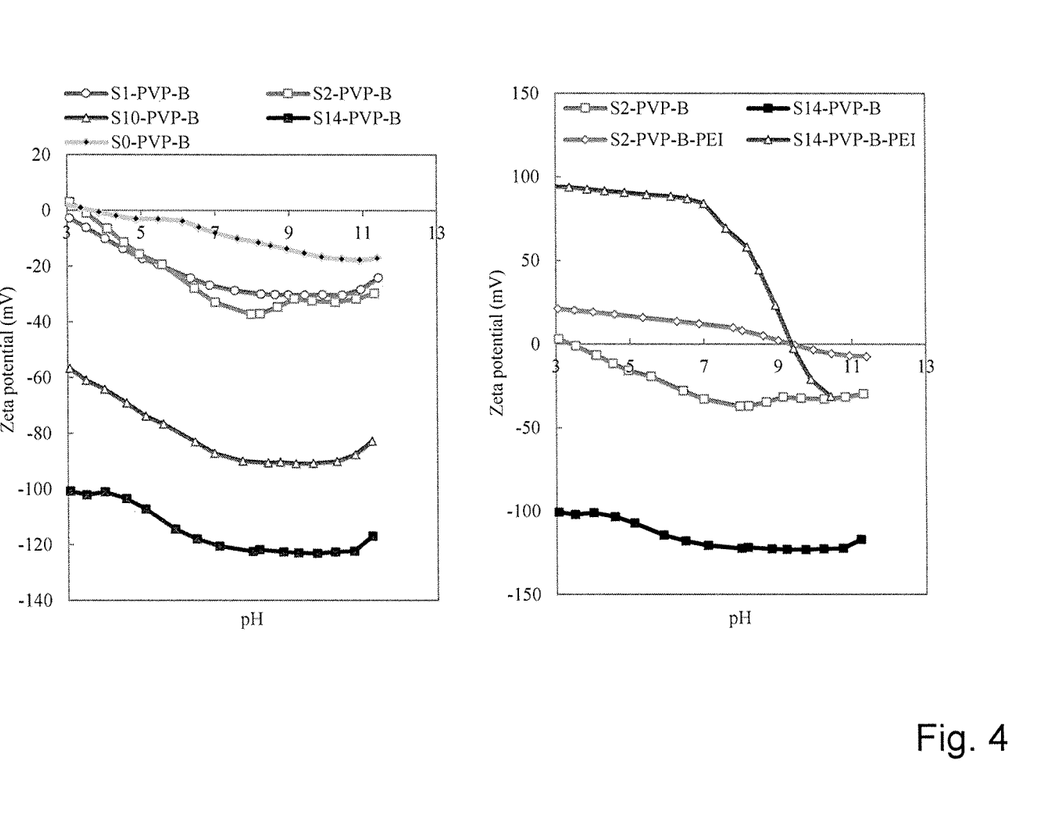
FIG. 4 is a pair of graphs depicting the zeta potential for the membranes of set 1 before and after LbL coating.

The membranes according to aspects of the invention were also characterized with an analysis of the surface charge (in particulars set 1) using zeta potential measurements, as shown in FIG. 4. FIG. 4 shows that a membrane made from a polymer with a higher sulfonation degree also results in an increase in the absolute zeta potential value as compared to reference membranes without sulfonated polymer or containing a polymer with a lower sulfonation degree. A higher sulfonation degree induces an increase in the negative net charge of the surface. As such, the presence of a higher charge density on the membrane surface understandably also results in the deposition of greater quantities of polyelectrolytes (at least for PEI, as shown in FIG. 4). Alternatively, a higher adsorbed PEI quantity—per area with a greater sulfonic acid density—could also result in a higher proportion of unbound amino groups (more loops).

Figure 5:
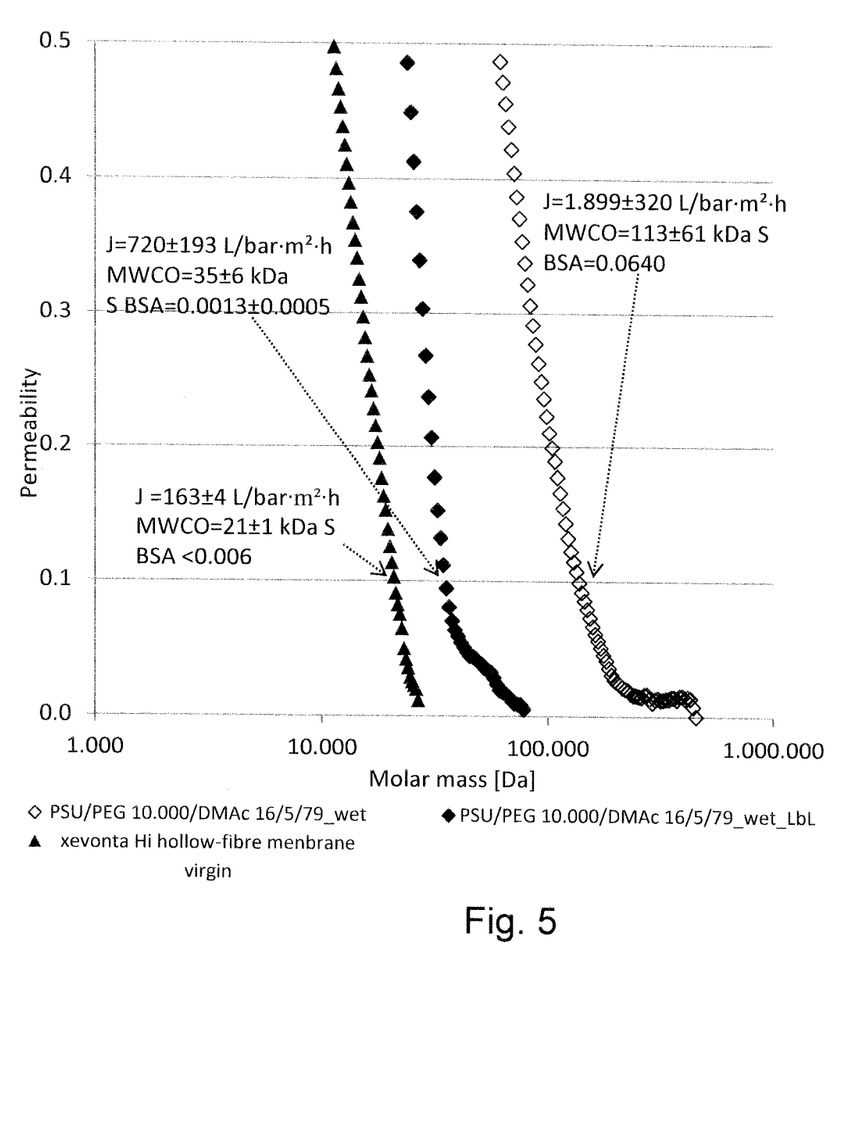
FIG. 5 is a graph depicting the molecular size cut-off limit for set 3, example P25, before and after LbL modification vs. commercial high-flux xevonta B. Braun membrane.

FIG. 5 additionally shows the dextran sieving curve before and after LbL modification of membrane P25 from set 4. As a result of LbL modification, the sieving curve clearly shifts into a smaller molar mass range. The curve apparently steepens up to a clear cut-off point. This suggests that the pore sizes are more narrowly distributed after modification. With a MWCO of 35±6 kDa, this shows a better performance for application in dialysis than a state-of-the-art xevonta Hi membrane, also in terms of water permeability (720±193 L*bar*h−1*m−2 vs. 163±4 L*bar*h−1*m−2) and sieving coefficient with BSA @ 22±2° C. (0.0013±0.0005 vs. <0.006). The base membrane is not suitable for application in dialysis, however (see FIG. 5).

Figure 6:
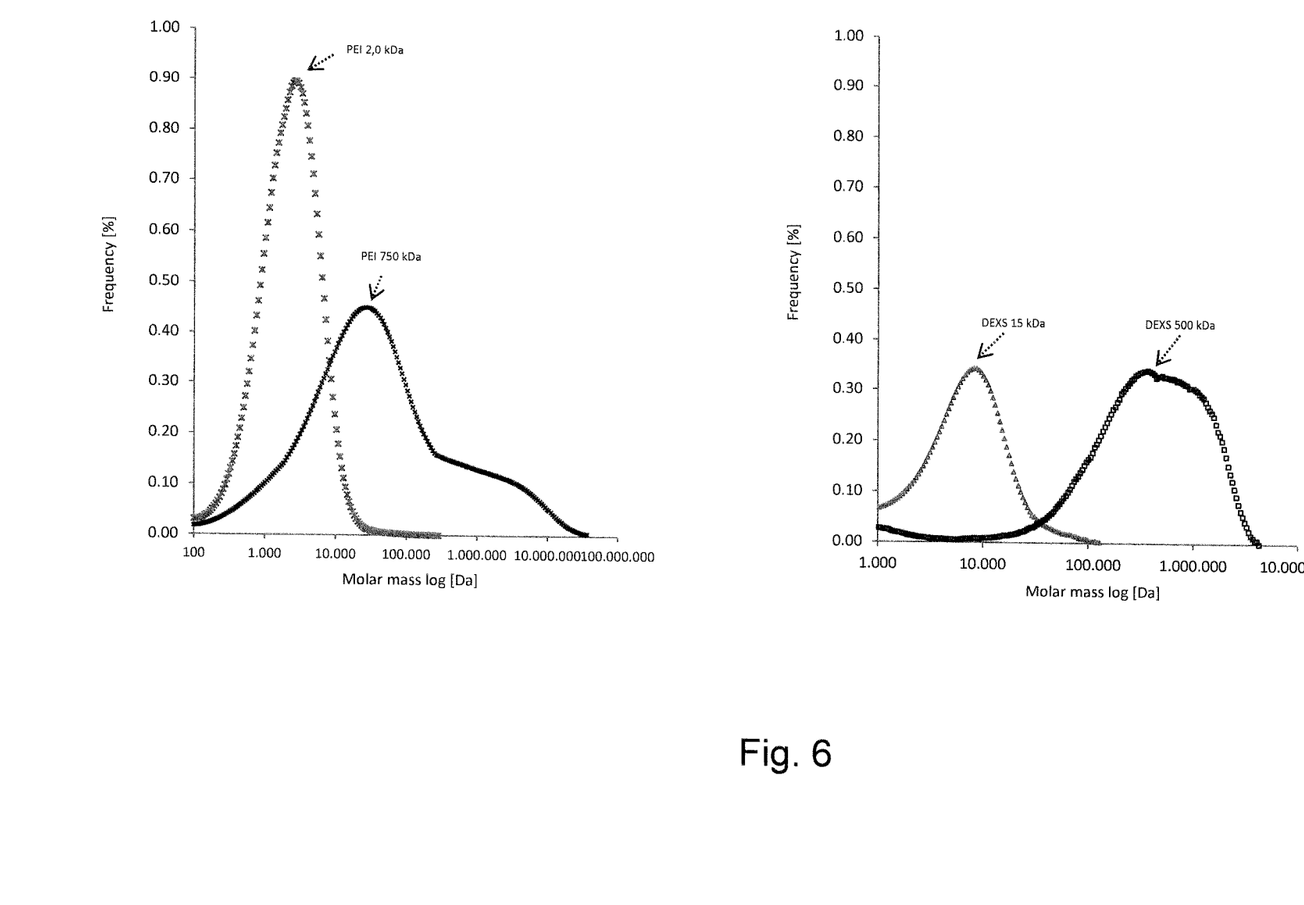
FIG. 6 is a pair of graphs depicting the molar mass distribution of the polymeric bonding agent PEI 2 kDa and 750 kDa ($M_w$) and the polysaccharides DEXS 15 kDa and 500 kDa, calculated using GPC.

Additionally, FIG. 6 shows molar mass distribution for PEI with 2.0 kDa and 750 kDa and DEXS with 15 kDa and 500 kDa, which are used for LbL modification. For PEI with 2.0 kDa, the molar mass is relatively narrowly distributed. In contrast to this, the molar mass for PEI with 750 kDa is broadly distributed with fractions across virtually the entire range, so that the distribution curves of PEI 750 kDa overlap with those of 2.0 kDa. This means that there are large proportions of small fractions. For DEXS, the distribution for 15 kDa is relatively narrow. A similar picture emerges for 500 kDa, with molar masses likewise relatively narrowly distributed. All in all, however, there is a low level of overlap compared with PEI.

The results also show that the water permeability, the MWCO and the sieving coefficient for BSA of the composite membranes can be adjusted selectively with the LbL coating. The membranes according to aspects of the invention obtained by LbL coating are therefore suitable for blood purification or dialysis.

For the purposes of the present invention it should be noted that the molecular mass measurements using gel permeation chromatography [GPC] were calibrated using PMMA standards for the molar mass range of 0.1 to 1200 kDa. With the GPC columns used, an approximately linear calibration function is obtained in the molar mass range of 0.5 to 1000 kDa, which is also very good for the analysis of oligomers

The invention claimed is:

1. A dialysis membrane in hollow-fiber membrane or flat membrane geometry comprising:
a composite assembled from:
at least one base membrane based on at least one polysulfone with at least one pore-forming hydrophilic additive, and
at least one functional layer arranged on the at least one base membrane, whereby the at least one functional layer is formed from at least one layer of a polymeric polycationic bonding agent and at least another layer of a polymeric polyanion,
wherein the base membrane is formed from a material which is selected from a group consisting of: a polysulfone, a sulfonated polysulfone, a polyethersulfone, a sulfonated polyethersulfone, a polyphenylsulfone, a sulfonated polyphenylsulfone, and mixtures thereof;
wherein the polymeric polycationic bonding agent is selected from a group consisting of: polyethylenimine, chitosan, polylysine, polyarginine, polyornithine, and mixtures thereof;
wherein the polymeric polyanion is a carboxylated polysaccharide or a sulfated polysaccharide which is selected from a group consisting of: a dextran sulfate with a molecular mass (Mw) of 15 kDa to 1 MDa, a sulfated chitosan with a molecular mass (Mw) of 30 kDa to 750 kDa, a cellulose sulfate with a molecular mass (Mw) of between 20 kDa and 1 MDa, and mixtures thereof; and
wherein the at least one pore-forming hydrophilic additive is selected from a group consisting of: polyvinylpyrrolidone, a short-chain glycol with 2 to 10 C atoms, triethylene glycol, propylene glycol, polyethylene glycol/polyethylene oxide, and mixtures thereof.

2. The dialysis membrane according to claim 1, wherein the sulfonated polysulfone exhibits at least one of a sulfonation degree of 0.1 to 20 weight %, in relation to the weight of the unsulfonated polysulfone;
the sulfonated polyethersulfone exhibits a sulfonation degree of 0.1 to 20 weight %, in relation to the weight of the unsulfonated polyethersulfone; or
the sulfonated polyphenylsulfone exhibits a sulfonation degree of 0.1 to 20 weight %, in relation to the weight of the unsulfonated polyphenylsulfone.

3. The dialysis membrane according to claim 2, wherein the sulfonated polysulfone exhibits a sulfonation degree of 9.3 or 13.4 weight %, in relation to the weight of the sulfonated polysulfone.

4. The dialysis membrane according to claim 2, wherein the sulfonated polyethersulfone exhibits a sulfonation degree of 1.1, 3.6, or 14.1 weight %, in relation to the weight of the unsulfonated polyethersulfone.

5. The dialysis membrane according to claim 2, wherein the sulfonated polyphenylsulfone exhibits a sulfonation degree of 1.0, 2.0, 10.1 or 14.7 weight %, in relation to the weight of the unsulfonated polyphenylsulfone.

6. The dialysis membrane according to claim 1, wherein the dialysis membrane exhibits a hydraulic permeability of 10 to 2,000 L/bar*h*m$^2$ and a sieving coefficient (@22±2°) for bovine serum albumin in the range of 0.0001 to 0.5 and a molecular mass cut-off value of 20 to 50 kDa.

7. The dialysis membrane according to claim 1, wherein the dialysis membrane exhibits a wall thickness of 20 to 200 μm.

8. The dialysis membrane according to claim 1, wherein the dialysis membrane exhibits a lumen diameter of 100 to 400 μm.

9. The dialysis membrane according to claim 1, wherein the cellulose sulfate has a molecular mass (Mw) of approximately 100 kDa.

10. A dialysis membrane module, wherein the module contains as filling dialysis membranes according to claim 1.

11. A dialysis membrane in hollow-fiber membrane or flat membrane geometry comprising:
a composite assembled from:
at least one base membrane, and
at least one functional layer arranged on the at least one base membrane, whereby the at least one functional layer is formed from at least one layer of a polymeric polycationic bonding agent and at least another layer of a polymeric polyanion,
wherein the base membrane is formed from a material comprising at least one polysulfone with at least one pore-forming hydrophilic additive and one or more of: a polyamide, a polyacrylonitrile, a polymethyl methacrylate, a polyacrylic acid, a polycarbonate, and a polyurethane;
wherein the polymeric polycationic bonding agent is selected from a group consisting of: polyethylenimine, chitosan, polylysine, polyarginine, polyornithine, and mixtures thereof;
wherein the polymeric polyanion is a carboxylated polysaccharide or a sulfated polysaccharide which is selected from a group consisting of: a dextran sulfate with a molecular mass (Mw) of 15 kDa to 1 MDa, a sulfated chitosan with a molecular mass (Mw) of 30 kDa to 750 kDa, a cellulose sulfate with a molecular mass (Mw) of between 20 kDa and 1 MDa, and mixtures thereof; and
wherein the at least one pore-forming hydrophilic additive is selected from a group consisting of: polyvinylpyrrolidone, a short-chain glycol with 2 to 10 C atoms, triethylene glycol, propylene glycol, polyethylene glycol/polyethylene oxide, and mixtures thereof.

* * * * *